United States Patent
Kuramori et al.

(10) Patent No.: US 7,854,166 B2
(45) Date of Patent: Dec. 21, 2010

(54) METHOD FOR EVALUATING AN INSTRUMENT OPERATING FORCE

(75) Inventors: Akira Kuramori, Kanagawa (JP); Masayoshi Kamijo, Nagano (JP); Tsugutake Sadoyama, Ibaraki (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 12/667,906

(22) PCT Filed: Jun. 24, 2008

(86) PCT No.: PCT/JP2008/061467

§ 371 (c)(1), (2), (4) Date: Feb. 4, 2010

(87) PCT Pub. No.: WO2009/008261

PCT Pub. Date: Jan. 15, 2009

(65) Prior Publication Data

US 2010/0139395 A1 Jun. 10, 2010

(30) Foreign Application Priority Data

Jul. 9, 2007 (JP) .............................. 2007-179624

(51) Int. Cl.
*A61B 5/22* (2006.01)
(52) U.S. Cl. .................................................. 73/379.01
(58) Field of Classification Search .............. 73/379.01; 601/5, 24
See application file for complete search history.

(56) References Cited

U.S. PATENT DOCUMENTS

| | | | |
|---|---|---|---|
| 4,742,832 A * | 5/1988 | Kauffmann et al. | 600/587 |
| 5,116,296 A * | 5/1992 | Watkins et al. | 482/91 |
| 7,396,337 B2 * | 7/2008 | McBean et al. | 601/5 |
| 7,532,925 B2 | 5/2009 | Kuramori et al. | |
| 7,617,762 B1 * | 11/2009 | Ragner | 92/37 |
| 2004/0082877 A1 | 4/2004 | Kouou et al. | |
| 2006/0079800 A1 | 4/2006 | Martikka et al. | |

FOREIGN PATENT DOCUMENTS

| | | |
|---|---|---|
| EP | 1 413 250 A1 | 4/2004 |
| EP | 1 535 570 A1 | 6/2005 |
| JP | 54-102079 A | 8/1979 |
| JP | 11-321671 A | 11/1999 |
| JP | 2003-177079 A | 6/2003 |
| JP | 2004-049622 A | 2/2004 |
| JP | 2004-344356 A | 12/2004 |

* cited by examiner

*Primary Examiner*—Jewel Thompson
(74) *Attorney, Agent, or Firm*—Carrier Blackman & Associates, P.C.; Joseph P. Carrier; William D. Blackman (57) ABSTRACT

Different loads are applied to the skeletal muscle of at least one of an upper arm, an upper limb girdle, and a lower limb of the test subject to cause isometric muscle contraction under each load and measure the muscle activity of the skeletal muscle. Then, an upper limit of the muscle activity in a region where a magnitude of the load and an intensity of the muscle activity have a linear relationship is determined as the limit in an appropriate muscle activity range that suits the test subject. Subsequently, the muscle activity of the skeletal muscle of a test subject operating an instrument is measured, and the test subject's force for operating the instrument is evaluated based on a frequency distribution where the frequency of the muscle activity of the skeletal muscle being exercised to operate the instrument is distributed with respect to the obtained limit.

10 Claims, 6 Drawing Sheets

METHOD FOR EVALUATING AN INSTRUMENT OPERATING FORCE

TECHNICAL FIELD

The present invention relates to an instrument operating force evaluation method for objectively evaluating an instrument operating force produced by a skeletal muscle of a test subject as the test subject operates an instrument and particularly to a method for evaluating an instrument operating force that permits easy evaluation of an instrument operating force by considering individual differences among test subjects.

BACKGROUND ART

Whether an operating force required to operate any of various instruments including the steering wheel of an automobile is appropriate for a driver's (operator's) specific force characteristic is conventionally evaluated based on the experiences of a person who provides an evaluation, in most cases by a sensory evaluation. Other evaluations include, for example, one of steering feeling using a myoelectric potential (see the Patent Document 1 and the Patent Document 2).

The Patent Document 1 describes an electric power steering apparatus. That document refers to a problem associated with prior art that a steering assist force is determined without considering the driver's human characteristic or, more specifically, the driver's force characteristic and, in addition, some drivers do not have a comfortable steering feeling. In order to solve the problem, the document describes an invention related to an electric power steering apparatus.

The electric power steering apparatus described in the Patent Document 1 produces the steering assist force using a torque generated by an electric motor and comprises force characteristic detecting means for detecting the driver's force characteristic and means for changing steering assist force generated by the electric motor according to the force characteristic detected by the force characteristic detecting means, whereby the force characteristic detecting means measures the load on a muscle of the driver through myoelectric measurement to determine the force characteristic.

According to the Patent Document 1, the steering assist force is changed according to the force characteristic that is detected as the driver's specific information. Thus, a steering assist force that best suits the driver can be imparted to the steering mechanism, and the driver can have a comfortable steering feeling.

The electric power steering apparatus described in the Patent Document 1 comprises a sensor for detecting the driver's force characteristic including electrodes disposed on the steering wheel and an impedance converter connected to the electrodes. When the driver holds the steering wheel, the palms of the driver's hands come into contact with the electrodes. The electric potential in the driver's body detected by the electrodes varies with the contact ratio, the contact pressure, etc. The driver's force characteristic is detected from the variation in the electric potential in his/her body.

The Patent Document 2 describes a steering feeling measuring apparatus for objectively and accurately evaluating the driver's steering feeling by differentiating between active steering and passive steering.

The steering feeling measuring apparatus described in the Patent Document 2 comprises first biological information detecting means for detecting first biological information produced by steering achieved as intended by the driver, second biological information detecting means for detecting second biological information that is other information than is produced by the steering achieved as intended by the driver, gathering means for gathering the first biological information detected by the first biological information detecting means and the second biological information detected by the second biological information detecting means by correlating the first biological information with the second biological information, and vehicle steering status detecting means for detecting the status of a steering mechanism of the vehicle driven by the driver. The gathering means further gathers information on the status of the vehicle steering mechanism together with the first biological information detected by the first biological information detecting means by correlating the information on the status of the vehicle steering mechanism with the first biological information. The first biological information is myoelectric potentials of the deltoid muscles and the second biological information is myoelectric potentials of the ulnar flexor muscles of wrist, pressures and slipping forces at given positions of both hands holding the steering wheel, etc.

[Patent Document 1] JP 11-321671 A
[Patent Document 2] JP 2003-177079 A

DISCLOSURE OF THE INVENTION

Problems to be Solved by the Invention

According to the Patent Document 1, however, the electrodes located on the steering wheel are fixed in position so that the positions at which the driver may hold the steering wheel are determined regardless of the driver's preference. Thus, a problem is posed that the driver cannot necessarily hold the steering wheel in the conditions he/she prefers.

In addition, which muscles are exercised depends on the positions at which the steering wheel is held so that an optimum steering assist force for a driver in one driving position is not necessarily optimal in another driving position. Therefore, the driver holding the steering wheel cannot always have a comfortable steering feeling in any given driving position.

In the Patent Document 2, the myoelectric potentials of the deltoid muscles are measured as first biological information, and the myoelectric potentials of the ulnar flexor muscles of wrist and the pressures and the slipping forces at given positions of both hands holding the steering wheel are measured as second biological information. Accordingly, the number of measuring sensors increases, and the amount of information to be processed also increases. Further, a plurality of pressure sensors need to be attached to both hands as illustrated in FIG. 2 of the Patent Document 2 in order to gather the second biological information. This poses a problem that a load is thereby applied to the driver. Thus, the steering feeling measuring apparatus described in the Patent Document 2 presents a problem of a complicated structure of the apparatus and cumbersome measurements.

An object of the present invention is to eliminate the problems associated with the prior art and provide a method for evaluating an instrument operating force that permits easy evaluation of an instrument operating force required to operate an instrument by considering individual differences among test subjects.

Means to Solve the Problems

To achieve the above objects, the present invention provides an evaluation method for evaluating an instrument operating force required to operate an instrument when a test subject operates the instrument, the evaluation being made specifically according to each test subject, the method comprising: a step of measuring, when applying different loads onto a skeletal muscle of at least one of an upper limb, an upper limb girdle, and a lower limb of the test subject to cause isometric muscle contraction, a muscle activity of the skeletal muscle observed under each of the different loads, a step of determining an upper limit of the muscle activity in a region where a magnitude of each of the applied different loads at a time of the isometric muscle contraction and an intensity of the muscle activity have a linear relationship as a limit of an appropriate muscle activity range that suits the test subject, a step of measuring a muscle activity of the skeletal muscle of the test subject during operation of the instrument, and a step of comparing a frequency distribution of the second muscle activity of the skeletal muscle during operation of the instrument with the limit and evaluating the instrument operating force required to operate the instrument according to the test subject.

When determining the limit, the limit is preferably obtained by determining the position at which a rate of change in gradient representing a change in magnitude of the muscle activity with respect to a change in each of the different loads exceeds a given value is obtained to determine a value of the muscle activity at the position as the limit.

Alternatively, when determining the limit, the limit may also be preferably obtained by approximating a first region with one straight line in a characteristic curve defined by the magnitude of each of the loads and the intensity of the muscle activity and approximating a second region, where each of the loads is greater than in the first region, with one curve to obtain a connection point where the approximated straight line and the approximated curve meet and determine a value of the muscle activity at the connection point as the limit.

The instrument operating force is evaluated preferably by comparing the frequency in a region of the frequency distribution where the muscle activity exceeds the limit and a frequency in a region of the frequency distribution where the muscle activity is lower than the limit with a given value.

Alternatively, the instrument operating force may also be preferably evaluated using a ratio of the frequency in a region of the frequency distribution where the muscle activity exceeds the limit to a frequency in a region of the frequency distribution where the muscle activity is lower than the limit.

When applying the different loads to cause the isometric muscle contraction, the magnitude of each of the different loads applied to the skeletal muscle of the test subject is increased gradually.

Preferably, a maximum of the myoelectric potential of the skeletal muscle measured is used as the muscle activity of the skeletal muscle.

Alternatively, the muscle activity of the skeletal muscle may also be preferably obtained by measuring the vibration of the skeletal muscle.

The operation of the instrument is, for example, operation of the steering wheel of an automobile, and each of the different loads is a steering torque applied to the steering wheel. When determining the upper limit, a region where each of the different loads provided by the steering torque is greater than 0.5 N·m is preferably obtained as the region where the linear relationship holds.

Effects of the Invention

According to the method for evaluating an instrument operating force of the invention, a plurality of different loads are applied to cause isometric muscle contraction with the respective loads and the muscle activity in a skeletal muscle is measured to determine an upper limit of the muscle activity in a region where the magnitude of the load and the intensity of the muscle activity have a linear relationship as a limit in an appropriate muscle activity range that suits the test subject. The distribution of the frequency of muscle activity in a skeletal muscle being exercised to operate an instrument with respect to the limit is considered by comparing the frequency distribution with the limit to evaluate the instrument operating force according to the test subject. This permits easy evaluation of the instrument operating force required to operate an instrument considering individual differences among test subjects.

LEGEND 10 test subject
12 elbow
14 shoulder
16 upper arm
18 forearm
20 hand
22 table
30, 30a sensors
32 amplifier
34, 52 myoelectric information acquiring unit
36, 56 data processors
37 input unit
38 display
40 evaluation system
42 measuring unit
44 steering wheel
45 steering shaft
46 motor
48 torque sensor
50 data processing unit
52 myoelectric information acquiring unit 54 torque information acquiring unit
56 data processor
58 evaluation unit
60 memory
62 CPU
64 motor control unit
70 external device

BEST MODE FOR CARRYING OUT THE INVENTION

The following describes in detail a method for evaluating an instrument operating force based on the embodiments shown in the accompanying drawings.

Figure 2:
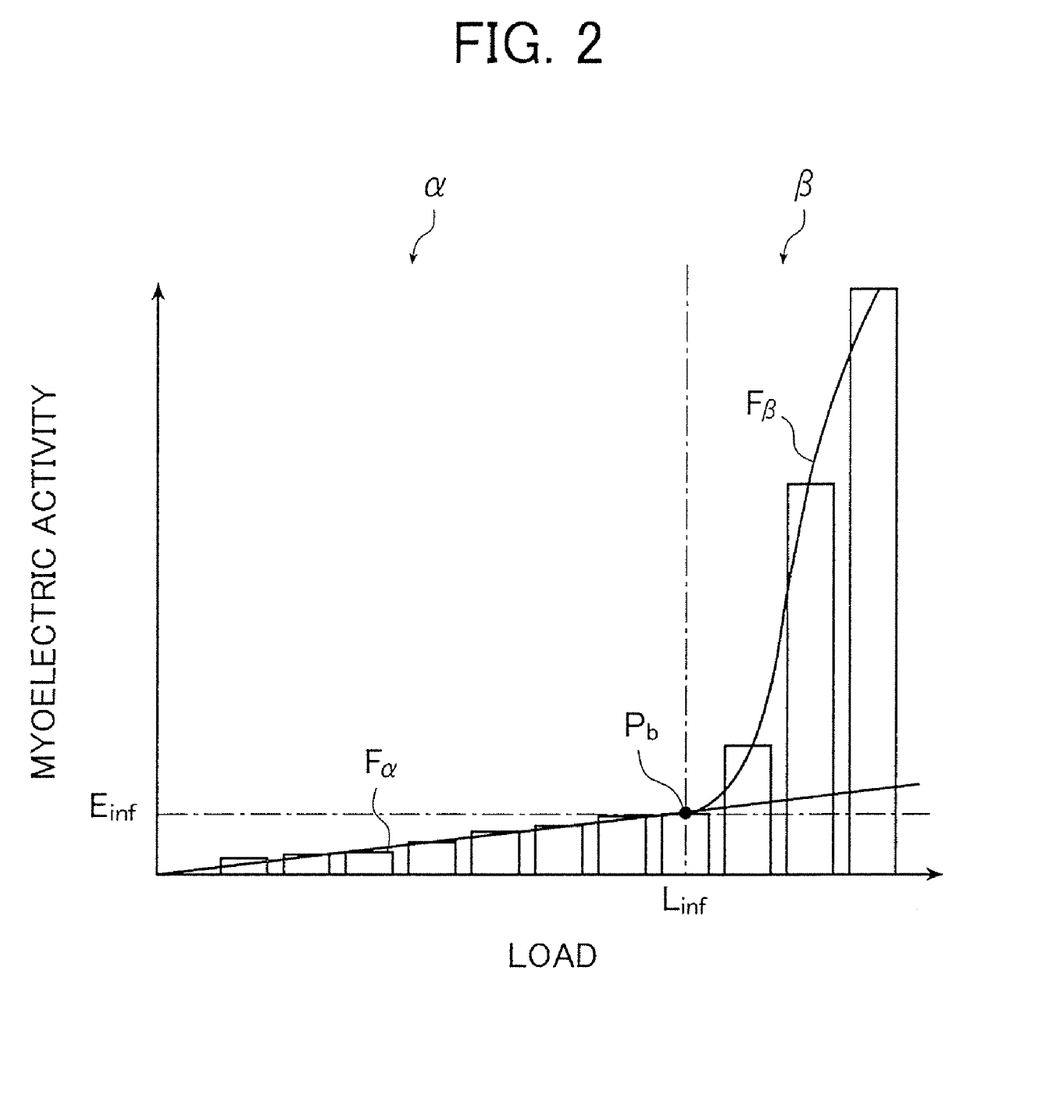
FIG. 2 is a graph representing a variation of muscle activity in response to load, where the vertical axis indicates muscle activity and the horizontal axis indicates load.

The inventors in the present application applied a plurality of different loads onto the skeletal muscle of at least one of an upper arm, a upper limb girdle, and a lower limb in order to cause isometric muscle contraction and measured the muscle activity of the skeletal muscle observed under the respective loads, obtaining the results as illustrated in FIG. 2 along with the following findings. The present invention uses the findings for evaluation of the instrument operating force.

First, the findings in the present invention will be described.

FIG. 1(a) is a schematic view for explaining a method for measuring the muscle activity of a skeletal muscle caused to produce isometric muscle contraction; FIG. 1(b) is a schematic view illustrating the position of a sensor when measuring the muscle activity of the skeletal muscle. Note that isometric muscle contraction is a muscle contraction in which the length of a muscle does not change because the force produced by the muscle contraction balances with the resistance force.

FIG. 2 is a graph representing a variation in muscle activity in response to a load, where the vertical axis indicates muscle activity and the horizontal axis indicates load.

When one skeletal muscle is caused to produce isometric muscle contraction, and the muscle activity of the skeletal muscle that is exercised as the load applied thereto is gradually increased is measured, the magnitude of the load and the intensity of the muscle activity have a linear relationship in one region and a non-linear relationship in another region as is apparent from FIG. 2. The inventors in the present invention know that the region where a linear relationship is observed is an appropriate region where the test subject can operate an instrument comfortably using his/her specific force characteristic.

The findings can be obtained by using the following system and method.

In the example illustrated in FIG. 1(a), the value of the myoelectric potential of the skeletal muscle of an upper limb, more specifically a biceps, of a test subject 10 is measured as muscle activity.

First, the test subject 10 has a shoulder 14 fixed in position with an elbow 12 placed on a table 22 while an upper arm 16 and a forearm 18 are kept in position to form a given angle with each other. In this status, a load L acts on a hand 20. Now, since the upper arm 16 and the forearm 18 are kept in position to form a given angle, the length of the biceps 16a of the upper arm 16 is fixed, and the biceps 16a of the upper arm 16 is caused to produce isometric muscle contraction.

Now, a sensor 30 for measuring a myoelectric potential is attached to the biceps 16a of the upper arm 16 as illustrated in FIG. 1(b). The sensor 30 is connected to an amplifier 32. The amplifier 32 is connected to a myoelectric information acquiring unit 34. The myoelectric information acquiring unit 34 is connected to a data processor 36. The data processor 36 is connected to an input unit 37 and a display 38.

The input unit 37 comprises a keyboard and a mouse and is used to enter data in a computer.

The display 38 displays information entered at the input unit 37 and information retained by the data processor 36. The display unit 38 may be any of a variety of monitors such as a CRT, an LCD, a PDP, and an organic EL.

The sensor 30 is a sensor for detecting the myoelectric potential of the biceps 16a of the test subject 10 and consists of a pair of dish-shaped Ag/AgCL electrodes. The pair of dish-shaped electrodes are attached to skin surface of the left upper arm 16 where the biceps 16a is located so that they are spaced apart a given distance, say several millimeters, e.g. 5 mm, from each other.

The electrodes of the sensor 30 are not limited to Ag/AgCL in material and may be made of other materials such as Ag or stainless steel.

When the electrodes of the sensor 30 are attached to the skin surface of the test subject 10, the electrodes of the sensor 30 are rubbed with a scrub and cleaned with alcohol to remove dirt using an electrode paste before being attached. The dirt is removed until the electric resistance is reduced to under 30 kΩ (preferably under 5 kΩ). The two electrodes are attached to the skin surface covering the muscle to be measured such that they are parallel with the muscle fibers.

Preferably, the two electrodes are attached to the skin surface covering the muscle so as to avoid the innervation band located close to the belly of the muscle to be measured or so as not to cross the innervation band.

The amplifier 32 is connected to the sensor 30 through lead wires; it is a known differential amplifier for amplifying the myoelectric potential detected by the sensor 30. Information on the myoelectric potential (active muscle potential information) of the biceps 16a detected by the sensor 30 and then amplified is supplied to the myoelectric information acquiring unit 34.

The myoelectric information acquiring unit 34 acquires in chronological order the active muscle potential information of the biceps 16a acquired by the sensor 30. The myoelectric information acquiring unit 34 samples and full-wave rectifies the active muscle potential information detected by the sensor 30 to produce a signal waveform (smoothed myoelectric waveform) of the myoelectric potential of the biceps 16a smoothed using a smoothing filter (low pass filter). Out of the myoelectric potential signal waveform (smoothed myoelectric waveform), the maximum of the myoelectric potential is sent to the data processor 36.

Weights each having a known mass are used as load L to obtain a maximum of the myoelectric potential for each of the weights having their respective masses. The mass of the weight used to measure the myoelectric potential is entered in the data processor 36 from the input unit 37. The data processor 36 correlates the mass of the weight or the load L with the myoelectric potential. As a result of the correlation thus established, a gradient representing the change in magnitude of muscle activity with respect to the change in load is obtained, and a processing is performed to calculate the rate of change in gradient with respect to the change in load. Alternatively, a curve fit is performed using a known function expression (one straight line, one curve).

Weights each having a known mass is used to provide the load L. Each of the weights having different masses is placed on the hand 20, with the mass increased sequentially to measure the muscle activity (myoelectric potential). The measurement is conducted in such a manner that the load L (mass of the weight) is sequentially increased until a condition is reached where, with the hand 20 holding the weight, the angle formed by the upper arm 16 and the forearm 18 can no longer be kept at a given angle, that is, where isometric muscle contraction becomes impossible. Thus, a result as illustrated in FIG. 2 is obtained.

As illustrated in FIG. 2, the muscle activity increases sharply as it exceeds a given load $L_{inf}$, so that the relationship of intensity of the muscle activity to magnitude of the load is no longer linear.

As illustrated in FIG. 2, the load can be divided into a region α and a region β at the load $L_{inf}$. The load and the muscle activity, represented by a straight line $F_α$, keep a linear relationship in the region α. On the other hand, the relationship in the region β, represented by a curve $F_β$, is not linear as the muscle activity sharply rises with the increase in load.

Thus, when an isometric muscle contraction is produced, a muscle activity $E_{inf}$ is obtained at a turnoff $P_b$ where the muscle activity sharply increases. Where the load is smaller than the load $L_{inf}$ at the turnoff $P_b$ illustrated in FIG. 2, the muscle will not be fatigued or only fatigued to a sufficiently low degree. In other words, the region a corresponds to an appropriate muscle activity range that suits the test subject's force characteristic; the muscle activity $E_{inf}$ corresponds to an upper limit in the region α and corresponds to a limit in the appropriate muscle activity range.

Where the load is greater than the load L at the turnoff $P_b$ illustrated in FIG. 2, the muscle will be fatigued so that a sufficient force cannot be generated. Therefore, the region β does not correspond to an appropriate muscle activity range that suits the test subject's force characteristic. The present invention focuses attention on the muscle activity $E_{inf}$ at the turnoff $P_b$ and uses the muscle activity $E_{inf}$ for evaluation of the instrument operating force.

Note that the invention may also be applied to a skeletal muscle of a upper limb girdle or a lower limb as well as a skeletal muscle of an upper limb (biceps).

In the case of an upper limb girdle (shoulder girdle), the myoelectric potential of a deltoid muscle, for example, is measured. In the case of a lower limb, the myoelectric potential of a quadriceps, for example, is measured.

Figure 1:
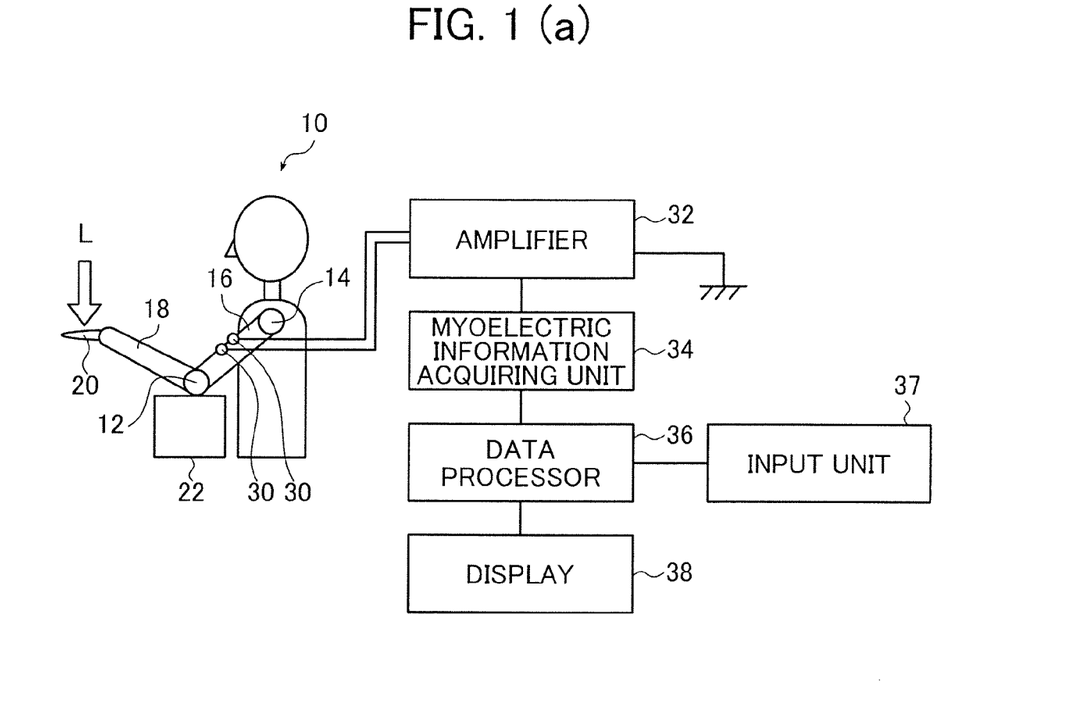
FIG. 1(a) is a schematic view for explaining a method for measuring the muscle activity of a biceps caused to produce isometric muscle contraction.
FIG. 1(b) is a schematic view illustrating the position of a sensor when measuring the muscle activity of the biceps.
Figure 3:
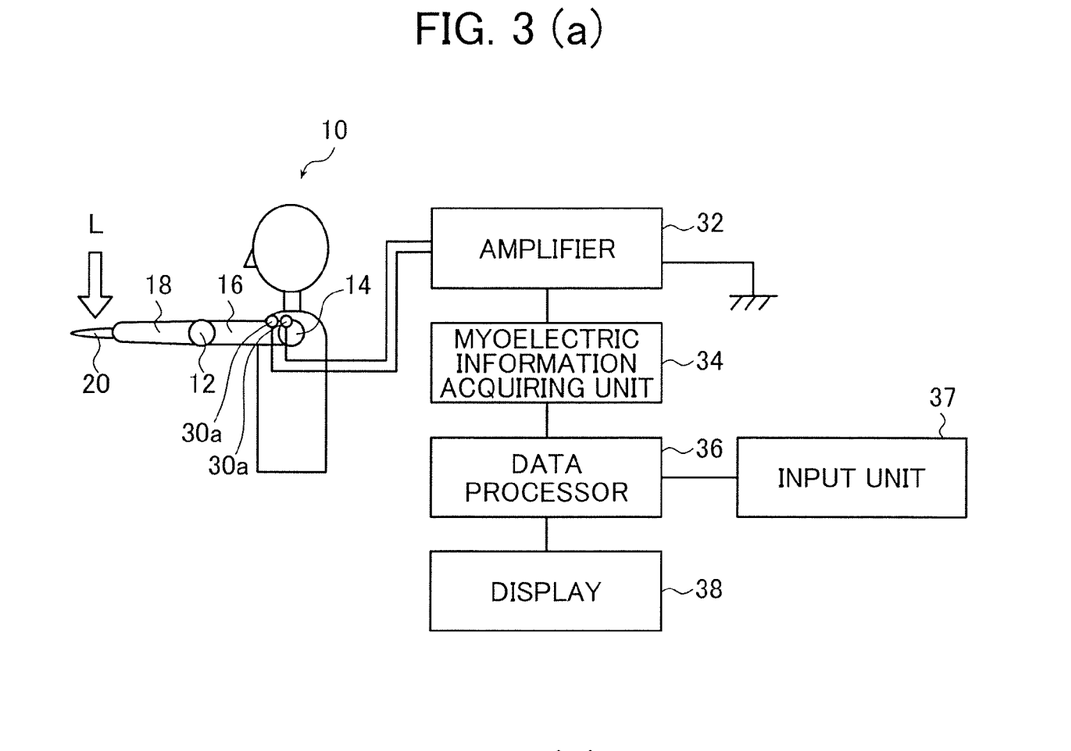
FIG. 3(a) is a schematic view for explaining a method for measuring the muscle activity of a deltoid muscle caused to produce isometric muscle contraction.
FIG. 3(b) is a schematic view illustrating the position of a sensor when measuring the muscle activity of the deltoid muscle.

When measuring the myoelectric potential of a deltoid muscle according to the invention, the only difference from the case of measuring the myoelectric potential of a biceps is the position where a sensor 30*a* is attached as illustrated in FIG. 3(*a*). Otherwise, the amplifier 32, the myoelectric information acquiring unit 34, the data processor 36, the input unit 37, and the display 38 have the same configuration as those illustrated in FIG. 1(*a*), and therefore a detailed description thereof will be omitted.

When measuring the myoelectric potential of a deltoid muscle according to the invention, the sensors 30*a* for measuring the myoelectric potentials of the deltoid muscle of the right shoulder (shoulder 14) and the deltoid muscle of the left shoulder (shoulder 14) of the test subject 10 are attached. The sensor 30*a* has the same configuration as the sensor 30. Each sensor 30*a* comprises a pair of dish-shaped Ag/AgCL electrodes, which are attached to a location of surface where the deltoid muscle is located, with a given distance, say several millimeters, e.g. 5 mm, from each other.

The electrodes of the sensor 30*a* are also not limited to Ag/AgCL in material and may be made of other materials such as Ag or stainless steel.

Each sensor 30*a* is attached to the skin surface of the test subject 10 in the same manner as the sensor 30 and, therefore, a detailed description thereof is omitted.

Each sensor 30*a* is attached to the shoulder 14 so that, as illustrated in FIG. 3(*b*), it is located in a position Y, which is spaced from an outer end X of the clavicle by a distance of three fingers in a longitudinal direction of the arm, with the electrodes spaced a given distance apart from each other. FIG. 3(*b*) illustrates a case where the sensor is attached to the right shoulder.

With the sensor 30*a* attached as described above, the upper arm 16 and the forearm 18 are kept so positioned as to form an angle of 180°, such that the arm is held in a horizontal position, and a weight having a known mass is placed in the hand 20 to apply a load thereby to measure the myoelectric potential of the deltoid muscle. Isometric muscle contraction can be thus induced in the deltoid muscles with the arms kept positioned horizontal.

The mass of the weight is changed to obtain a maximum of the myoelectric potential of each deltoid muscle for each mass of the weight, whereupon the load and the myoelectric potential are correlated to produce a graph as illustrated in FIG. 2. Then the turnoff $P_b$ is determined where the muscle activity increases sharply as the applied load exceeds a given load $L_{inf}$ so that the linear relationship no longer holds. Finally obtained is the muscle activity $E_{inf}$ of the deltoid muscle at the turnoff $P_b$. According to the invention, the muscle activity $E_{inf}$ of the deltoid muscle may also be used to evaluate the instrument operating force factoring in the test subject's force characteristic as in the case of the biceps 16*a*.

Although the myoelectric potential is used above to obtain the muscle activity, the present invention is not limited thereto; the muscle activity $E_{inf}$ may be obtained by measuring vibration produced in a skeletal muscle as well as by using the myoelectric potential. The vibration produced in a skeletal muscle may be measured using a remote instrument such as a Doppler vibrometer. Further, the muscle activity $E_{inf}$ may be obtained by measuring vibration produced in a skeletal muscle as muscle sound.

Now, the method for evaluating an instrument operating force according to the present invention will be described.

Figure 4:
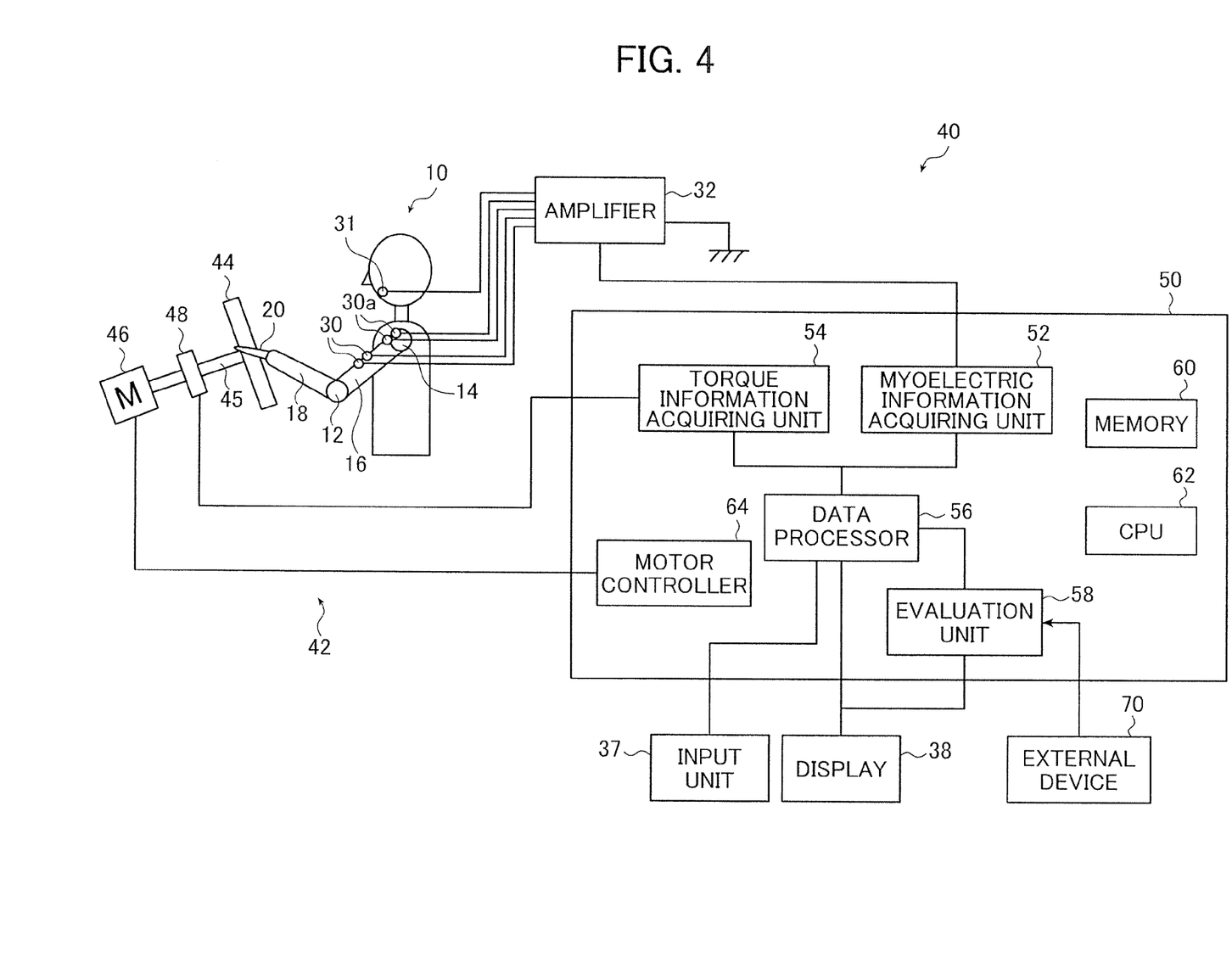
FIG. 4 is a schematic view illustrating an embodiment of an evaluation system used for implementing the method for evaluating an instrument operating force according to the invention.

FIG. 4 is a schematic view illustrating an embodiment of the evaluation system used for implementing the method for evaluating an instrument operating force according to the invention. In an evaluation system 40 illustrated in FIG. 4, the same components as those illustrated in FIG. 1 used for measuring the myoelectric potential are assigned like reference characters, and a detailed description thereof will be omitted.

The evaluation system 40 illustrated in FIG. 4 will be explained by taking a steering wheel 44 of an automobile as an example of instrument, but the invention is not limited thereto.

The evaluation system 40 comprises a measuring unit 42, a data processing unit 50, the input unit 37, and the display 38.

The evaluation system 40 is provided with a seat, not shown, to permit assuming a position for driving an automobile.

The measuring unit 42 comprises the sensor 30 for detecting the active muscle potential (referred to as myoelectric potential below) of a biceps of the test subject 10, the sensors 30*a* for detecting the myoelectric potentials of the left and right deltoid muscles, an electrode 31 acting as earth electrode, and an amplifier 32 connected to the sensors 30, 30*a* and the electrode 31.

The measuring unit 42 further comprises a motor 46 for turning a steering shaft 45 attached to the steering wheel 44, and a torque sensor 48 for detecting the torque produced about the steering shaft 45 by the rotation of the steering wheel 44 caused by the motor 46.

The left and right deltoid muscles of the test subject 10 are muscles related to the steering of the automobile and are exercised as the test subject 10 turns the steering wheel 44.

As described above, the sensor 30 is a sensor for detecting the myoelectric potential of the biceps 16a (see FIG. 1(b)) of the test subject 10.

As described above, the sensors 30a are sensors for detecting the myoelectric potentials of the deltoid muscle of the right shoulder (shoulder 14) and the deltoid muscle of the left shoulder (shoulder 14) of the test subject 10 and have the same configuration as the sensor 30.

The electrode 31 is an earth electrode attached to an ear lobe of the test subject 10, which is an electrically inactive position, to keep the potential of the test subject 10 at a constant level in order to permit accurate measuring with the sensors 30 and 30a. The electrode 31 connected to the amplifier 32 is grounded through the amplifier 32.

The amplifier 32 is connected through lead wires to the detection sensors 30, 30a and the electrode 31; it is a known differential amplifier for amplifying the myoelectric potential detected by the sensors 30, 30a.

The information on the left and right myoelectric potentials (active muscle potential information) detected by the sensors 30, 30a and then amplified is each sent to the myoelectric information acquiring unit 34 of the data processor 40.

The motor 46 is a drive unit for turning the steering shaft 45. The motor 46 is connected to a motor controller 64 of the data processing unit 50.

The torque sensor 48 acquires information on the magnitude of the rotary torque (referred to as steering torque below) about the steering shaft 45 and information on the direction of rotation of the steering shaft 45. The torque sensor 48 may be a known torque sensor such as one used for the power steering system in an automobile.

The evaluation system 40 according to the invention permits obtaining the myoelectric potential of an upper limb (myoelectric potential of a biceps) and the myoelectric potentials of the upper limb girdles (myoelectric potentials of the deltoid muscles) for evaluating the force for operating the steering wheel 44 with the test subject 10 assuming a position for driving an automobile.

The data processing unit 50 comprises a myoelectric information acquiring unit 52, a torque information acquiring unit 54, a data processor 56, an evaluation unit 58, a memory 60, a CPU 62, and the motor controller 64. The data processing unit 50 is a computer whose components function as the CPU 62 executes a program stored in the memory 60. The data processing unit 50 may be a dedicated device whose components are configured by dedicated circuits.

The myoelectric information acquiring unit 52 has the same configuration as the myoelectric information acquiring unit 34 illustrated in FIG. 1(a), and therefore a detailed description thereof will be omitted. The myoelectric information acquiring unit 52 is connected to the data processor 56.

The torque information acquiring unit 54 is connected to the torque sensor 48. The steering torque produced by the rotation of the motor 46 is detected by the torque sensor 48, whose output signal is supplied to the torque information acquiring unit 54. The torque information acquiring unit 54 calculates the value of the steering torque based on the output signal of the torque sensor 48. The torque information acquiring unit 54 is connected to the data processor 56.

The data processor 56 correlates the value of the steering torque and the myoelectric potential. In addition, the data processor 56 obtains the muscle activity $E_{inf}$ based on, for example, the correlation established between the value of the steering torque and the myoelectric potential.

As described above, the muscle activity $E_{inf}$ is obtained by determining the turnoff $P_b$ illustrated in FIG. 2. The turnoff $P_b$ is determined from the correlation between the value of the steering torque and the myoelectric potential as a position where, for example, the rate of change in gradient representing the change in magnitude of the myoelectric potential with respect to the change in magnitude of the steering torque exceeds a given value. The muscle activity ($E_{inf}$) at this position is determined as the limit in an appropriate muscle activity range that suits the test subject's force characteristic. Alternatively, in the characteristic curve defined by the magnitude of the steering torque and the intensity of the muscle activity, the curve in a first region is approximated by one straight line, and the curve in a second region where the steering torque is greater than in the first region is approximated by one curve to obtain a connection point where the straight line and the curve meet. The muscle activity ($E_{inf}$) at the connection point is determined as an upper limit in the first region and as a limit in the appropriate muscle activity range that suits the test subject's force characteristic.

Such a position at the upper limit in the range in which the magnitude of the muscle activity with respect to the steering torque has a linearity is determined as the turnoff $P_b$.

In a region where the load is extremely small, for example, a region where the steering torque is not greater than 0.5 N·m or not greater than a range of 0.5 to 1.0 N·m, the friction or the hysteresis in the steering system causes the measurement of the muscle activity to lose sufficient accuracy. Accordingly, the above region where the load is extremely small is preferably excluded from the region used when obtaining the turnoff $P_b$.

The evaluation unit 58, connected to the data processor 56, uses the muscle activity $E_{inf}$ obtained by the data processor 56 to evaluate the instrument operating force as will be described. The evaluation unit 58 is connected to external device 70. The external device 70 is used to enter a method for evaluating the instrument operating force, etc.

The data processor 56 is connected to the display 38. The display 38 displays a graph representing a correlation between value of the steering torque obtained by the data processor 56 and myoelectric potential, the value of the turnoff $P_b$, etc.

The motor controller 64 controls the motor 46 for turning the steering 44.

Now, the method for evaluating the instrument operating force according to the embodiment will be described.

First, the sensor 30 is attached to the skin surface corresponding to the biceps of the upper arm 16 of the test subject 10, and the sensors 30a are attached to the skin surfaces corresponding to the deltoid muscles of the shoulders 14.

The test subject 10 sits on a seat to assume a driving position. Now, the test subject 10 holds the steering wheel 44 in a neutral position so as not to turn the steering wheel 44.

Then, the motor controller 64 turns on the motor 46 in order to turn the steering shaft 45. Accordingly, the test subject provides a steering torque to the steering wheel 44 to resist the rotation of the steering wheel 44. Thus, a load is applied to the hand 20 of the test subject 10. The steering torque is detected by the torque sensor 48, and the value of the steering torque is obtained by the torque information acquiring unit 54.

At the same time, the myoelectric potential of the biceps is measured by the sensor 30, and the myoelectric potentials of the deltoid muscles are measured by the sensors 30a. From the measurement results given by the sensors 30, 30a, the myoelectric information acquiring unit 52 works out a maximum of the myoelectric potential of the biceps and maxima of the myoelectric potentials of the deltoid muscles.

The measurement of the steering torque and the calculation of a maximum of the myoelectric potential of the biceps and the maxima of the myoelectric potentials of the deltoid muscles are performed a plurality of times by changing the value of the rotary torque of the motor 46 through the control by the motor controller 64.

When the test subject 10 in a driving position is holding the steering wheel 44 at a given angle so that it is kept from turning, it may be assumed that isometric muscle contraction is being produced in the skeletal muscles of the test subject 10. In other words, it may be assumed that isometric muscle contraction is being produced in the biceps and the deltoid muscles under measurement.

The data processor 56 correlates the maximum of the myoelectric potential of the biceps and the maxima of the myoelectric potentials of the deltoid muscles with the value of the steering torque. Further, as illustrated in FIGS. 5(a) and (b), the turnoffs $P_b$ are determined by the above methods for the biceps and the deltoid muscles, and the respective muscle activities $E_{inf}$ are obtained.

Figure 5:
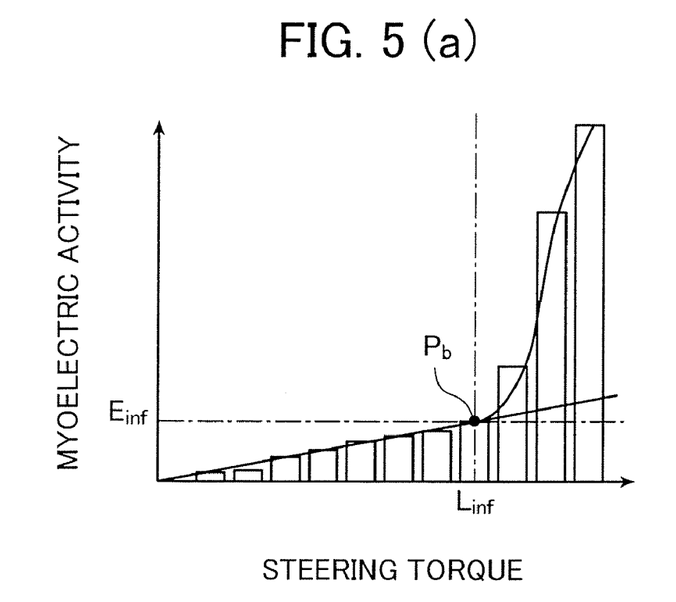
FIG. 5(a) is a graph representing a relationship between muscle activity of a biceps and steering torque, where the vertical axis indicates muscle activity and the horizontal axis indicates steering torque.
FIG. 5(b) is a graph representing a relationship between muscle activity of a deltoid muscle and steering torque, where the vertical axis indicates muscle activity and the horizontal axis indicates steering torque.

FIG. 5(a) illustrates a relationship between muscle activity of the biceps and steering torque; FIG. 5(b) illustrates a relationship between muscle activities of the deltoid muscles and steering torque.

Next, the test subject 10, keeping the above driving position, is allowed to operate the individual steering wheels each having a given power steering characteristic. In the process, the myoelectric potentials of the biceps and the deltoid muscles of the test subject 10 are measured while the instrument is being operated. Thus, frequency distributions of myoelectric potentials of the biceps and the deltoid muscles measured while the instrument is being operated are obtained, whereupon the frequency distributions and the muscle activities $E_{inf}$ are compared to evaluate an instrument operating force required to operate the instrument according to the test subject 10.

Figure 6:
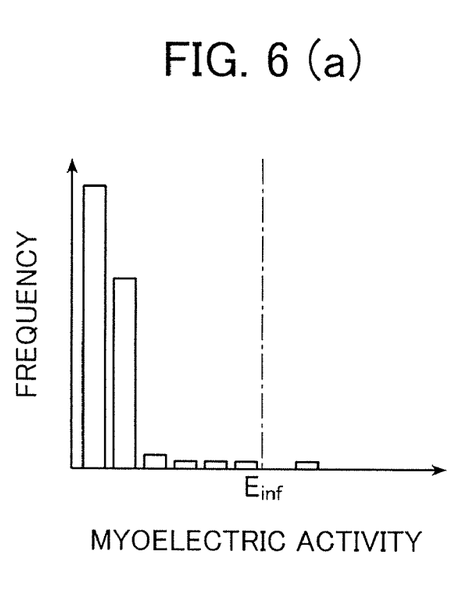
FIGS. 6(a) to 6(c) are graphs each representing a muscle activity frequency distribution obtained with a power steering provided having a characteristic of A to C, respectively, where the vertical axis indicates degree and the horizontal axis indicates muscle activity.

FIGS. 6(a), (b), and (c) each illustrate a frequency distribution of the myoelectric potential and a muscle activity $E_{inf}$ obtained respectively when the test subject 10, keeping the driving position, operates the individual steering wheels having different characteristics: a characteristic A, a characteristic B, and a characteristic C. In this case, the myoelectric potential of the biceps and the myoelectric potentials of the deltoid muscles are measured for the three different characteristics A, B, and C.

With the power steering having the characteristic A illustrated in FIG. 6(a), the frequency is higher than a given value in a region where the muscle activity is lower than the muscle activity $E_{inf}$. With the characteristic A, the evaluation unit 58 determines that the test subject 10, feeling little load, feels that the resistance is too small.

With the power steering having the characteristic B illustrated in FIG. 6(b), the frequency is higher than a given value in a region where the muscle activity is lower than the muscle activity $E_{inf}$, whereas the frequency is lower than a given value in a region where the muscle activity is higher than the muscle activity $E_{inf}$. With the characteristic B, the evaluation unit 58 determines that the test subject 10, feeling an appropriate degree of load, is feeling an appropriate degree of resistance.

With the power steering having the characteristic C illustrated in FIG. 6(c), the frequency is higher than a given value in a region where the muscle activity is lower than the muscle activity $E_{inf}$, and the frequency is also higher than a given value in a region where the muscle activity is higher than the muscle activity $E_{inf}$. With the characteristic C, the evaluation unit 58 determines that the test subject 10, feeling a great load, feels that the resistance is too great.

Thus, the instrument operating force required to operate the instrument can be evaluated for the three different power steering characteristics A, B, and C using the muscle activity $E_{inf}$ specific to the test subject 10.

Thus, according to the invention, the muscle activity $E_{inf}$ is obtained with the test subject assuming the same position as his/her driving position, whereupon the muscle activity $E_{inf}$ is used to evaluate the instrument operating force required to operate the instrument factoring in the individual difference of the test subject 10. Further, the invention, requiring only the measurement of the myoelectric potentials and the load, eliminates the need for troublesome work of, for example, attaching various sensors such as a pressure sensor as was conventionally the case and thus facilitates measurement.

The evaluation by the evaluation unit 58 may also be achieved based on the ratio of the frequency in a region where the muscle activity is lower than a threshold defined by the muscle activity $E_{inf}$ to the frequency in a region where the muscle activity is higher than the muscle activity $E_{inf}$. Alternatively, the evaluation unit 58 may base its evaluation on the distribution profile of the frequency distribution of the myoelectric potential. Alternatively, the evaluation unit 58 may use the frequency in a region where the muscle activity is higher than the muscle activity $E_{inf}$ to perform evaluation.

According to the invention, the results illustrated in FIGS. 5(a) and (b) may be used for evaluation of forces and torques produced on the steering wheel in cases where, for example, the tires are caught in ruts when the automobile is moving. The results may be further used for evaluation of operating forces required to operate the handles of, for example, machine tools.

Although the myoelectric potential is used to obtain the muscle activity, the present invention is not limited thereto; the muscle activity $E_{inf}$ may also be obtained as well by measuring vibration produced in a skeletal muscle as by using the myoelectric potential. Needless to say, the muscle activity $E_{inf}$ may be used to evaluate the above instruments.

While the method for evaluating the instrument operating force according to the present invention has been described in detail above, the present invention is not limited to the above embodiments, and various improvements and modifications may be made without departing from the spirit and scope of the invention.

The invention claimed is:

1. An instrument operating force evaluation method for evaluating an instrument operating force required to operate an instrument when a test subject operates the instrument, the evaluation being made specifically according to a test subject, the method comprising:

a step of measuring, when applying different loads onto a skeletal muscle of at least one of an upper limb, an upper limb girdle, and a lower limb of the test subject to cause isometric muscle contraction, a first muscle activity of the skeletal muscle observed under each of the different loads, a step of determining an upper limit of the first muscle activity in a region where a magnitude of each of the different loads at a time of the isometric muscle contraction and an intensity of the first muscle activity have a linear relationship as a limit of an appropriate muscle activity range that suits the test subject, a step of measuring a second muscle activity of the skeletal muscle of the test subject operating the instrument, and a step of comparing a frequency distribution of the second muscle activity of the skeletal muscle being exercised for operation of the instrument with the limit and evaluating the instrument operating force required to operate the instrument according to the test subject.

2. The instrument operating force evaluation method according to claim 1, wherein, when determining the limit, a position at which a rate of change in gradient representing a change in magnitude of the first muscle activity with respect to a change in each of the different loads exceeds a given value is obtained to determine a value of the first muscle activity at the position as the limit.

3. The instrument operating force evaluation method according to claim 1, wherein, when determining the limit, in a characteristic curve defined by the magnitude of each of the different loads and the intensity of the first muscle activity, a first region is approximated by one straight line, and a second region where each of the different loads is greater than in the first region is approximated by one curve to obtain a connection point where the approximated straight line and the approximated curve meet and determine a value of the first muscle activity at the connection point as the limit.

4. The instrument operating force evaluation method according to claim 1, wherein a frequency in a region of the frequency distribution where the second muscle activity exceeds the limit and a frequency in a region of the frequency distribution where the second muscle activity is lower than the limit are compared with a given value to evaluate the instrument operating force.

5. The instrument operating force evaluation method according to claim 1, wherein the instrument operating force is evaluated using a ratio of a frequency in a region of the frequency distribution where the second muscle activity exceeds the limit to a frequency in a region of the frequency distribution where the second muscle activity is lower than the limit.

6. The instrument operating force evaluation method according to claim 1, wherein when applying the different loads to cause the isometric muscle contraction, the magnitude of each of the different loads applied to the skeletal muscle of the test subject is increased gradually.

7. The instrument operating force evaluation method according to claim 1, wherein a myoelectric potential of the skeletal muscle is measured, and a maximum of the myoelectric potential for each of the different loads is used as the first muscle activity of the skeletal muscle and the second muscle activity of the skeletal muscle.

8. The instrument operating force evaluation method according to claim 1, wherein the first muscle activity of the skeletal muscle and the second muscle activity of the skeletal muscle are obtained by measuring vibration of the skeletal muscle.

9. The instrument operating force evaluation method according to claim 1, wherein the operation of the instrument is operation of a steering wheel of an automobile, and each of the different loads is a steering torque applied to the steering wheel.

10. The instrument operating force evaluation method according to claim 9, wherein, when determining the upper limit, a region where each of the different loads provided by the steering torque is greater than 0.5 N·m is obtained as the region where the linear relationship holds.

* * * * *